United States Patent [19]

Wirth et al.

[11] Patent Number: 5,892,051

[45] Date of Patent: Apr. 6, 1999

[54] ADDITIVES FOR LUBRICANTS

[75] Inventors: Hermann O. Wirth, Bensheim; Hans-Helmut Friedrich, Lautertal, both of Germany

[73] Assignee: Ciba Specialty Chemicals Corporation, Tarrytown, N.Y.

[21] Appl. No.: 769,678

[22] Filed: Dec. 16, 1996

Related U.S. Application Data

[62] Division of Ser. No. 422,670, Apr. 12, 1995, Pat. No. 5,618,778, which is a continuation of Ser. No. 999,173, Dec. 28, 1992, abandoned, which is a continuation of Ser. No. 825,437, Jan. 23, 1992, abandoned, which is a continuation of Ser. No. 717,163, Jun. 17, 1991, abandoned, which is a continuation of Ser. No. 107,896, Oct. 9, 1987, abandoned, which is a continuation of Ser. No. 23,939, Mar. 5, 1987, abandoned, which is a continuation of Ser. No. 894,460, Jul. 30, 1986, abandoned, which is a continuation of Ser. No. 750,839, Jul. 1, 1985, abandoned.

[30] Foreign Application Priority Data

Jun. 29, 1984 [CH] Switzerland ............... 3148/84
May 14, 1985 [CH] Switzerland ............... 2047/85

[51] Int. Cl.$^6$ ............... C07D 277/62; C07C 319/00
[52] U.S. Cl. ............... 548/165; 548/179; 568/50
[58] Field of Search ............... 508/274, 277, 508/431, 432, 501, 519, 547, 562, 570, 571; 548/165, 179; 568/50

[56] References Cited

U.S. PATENT DOCUMENTS

| | | | |
|---|---|---|---|
| 2,434,099 | 1/1948 | Bousquest | 549/556 |
| 2,492,335 | 12/1949 | Chenicek et al. | 252/482 |
| 2,731,437 | 1/1956 | Bender et al. | 549/574 |
| 2,965,652 | 12/1960 | Gaertner | 260/348.6 |
| 3,330,804 | 7/1967 | O'Shea | 252/48.2 |
| 3,399,041 | 8/1968 | McCabe | 252/475 |
| 3,876,550 | 4/1975 | Holubec | 252/475 |
| 3,954,839 | 5/1976 | Dexter et al. | 260/73 |
| 3,987,086 | 10/1976 | Dexter et al. | 260/473 |
| 4,031,023 | 6/1977 | Musser et al. | 252/48.2 |
| 4,071,497 | 1/1978 | Dexter et al. | 260/45.85 |
| 4,085,502 | 4/1978 | Dexter et al. | 260/424 |
| 4,147,666 | 4/1979 | Michaelis et al. | 252/48.2 |
| 4,209,410 | 6/1980 | Baldwin et al. | 252/48.2 |
| 4,217,233 | 8/1980 | Michaelis | 252/475 |
| 4,244,827 | 1/1981 | Michaelis et al. | 252/46.4 |
| 4,246,127 | 1/1981 | Michaelis et al. | 252/482 |
| 4,260,503 | 4/1981 | Michaelis | 252/47.5 |
| 4,279,761 | 7/1981 | Michaelis et al. | 252/46.4 |
| 4,284,573 | 8/1981 | Arnett et al. | 260/348.5 |
| 4,284,574 | 8/1981 | Bagga | 549/555 |
| 4,362,887 | 12/1982 | Kline | 560/152 |
| 4,373,073 | 2/1983 | Waitech et al. | 549/517 |
| 4,540,802 | 9/1985 | Tomita et al. | 549/557 |
| 4,621,098 | 11/1986 | Umminger et al. | 514/562 |
| 4,772,405 | 9/1988 | Wirth | 252/78.1 |
| 4,835,310 | 5/1989 | Wirth et al. | 508/570 |
| 5,002,698 | 3/1991 | Wirth et al. | 508/258 |
| 5,026,865 | 6/1991 | Karol | 548/142 |
| 5,284,592 | 2/1994 | Aberkane et al. | 560/195 |
| 5,618,778 | 4/1997 | Wirth et al. | 508/274 |

OTHER PUBLICATIONS

Chem. Abst. vol. 70 (1969), 36713u (Month unknown).
Prisadki. Smaz. Maslam (Vop. Sin, Issled Prinen. Prisadek, Maslam, Topl. Palim. Mater.) 251–65/
Chem. Abst. vol. 79, (1973) 115348 + Month Unknown.
Chem. Abst. vol. 88, 137448 p (1978) (Month Unknown).
A.R. Derzkinskii et al. Inzvest. Akad. (Month Uknown) Nauk. SSSR, vol. 6, 1384 (1984) English Trans. Provided.

*Primary Examiner*—Margaret Medley
*Attorney, Agent, or Firm*—Luther A. R. Hall; Victoria M. Malia

[57] ABSTRACT

Compounds of formula I,

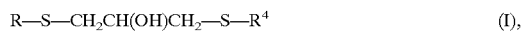

$$R-S-CH_2CH(OH)CH_2-S-R^4 \qquad (I),$$

where R is tert-alkyl of 4 to 20 carbon atoms and 4 is benzothiazolyl, $-(CH_2)_m-S-CH_2CH(OH)CH_2-S-(C_1-C_{16}alkyl)$, m is 0, or $-(CH_2)_s-R^7$ where s is 1 to 4 and $R^7$ is benzothiazolyl are effective additives for lubricants, hydraulic fluids or other lubricant systems. Some novel compounds of formula I are claimed.

4 Claims, No Drawings

ADDITIVES FOR LUBRICANTS

This is a DIVISIONAL of application Ser. No. 08/422,670 filed Apr. 12, 1995, now U.S. Pat. No. 5,618,778, which is a CONTINUATION of application Ser. No. 07/999,173 filed Dec. 28, 1992 now abandoned, which is a CONTINUATION application Ser. No. 07/825,437 filed Jan. 23, 1992 now abandoned, which is a CONTINUATION application Ser. No. 07/717,163 filed Jun. 17, 1991, now abandoned, which is a CONTINUATION application Ser. No. 07/107,896, filed Oct. 9, 1987, now abandoned, which is a CONTINUATION application Ser. No. 07/023,939 filed Mar. 5, 1987, now abandoned, which is a CONTINUATION application Ser. No. 06/894,460, filed Jul. 30, 1986, now abandoned, which is a CONTINUATION application Ser. No. 06/750,839, filed Jul. 1, 1985, now abandoned.

The present invention relates to lubricants and hydraulic fluids which contain compounds having thioether groups, to the use of these compounds as additives, and to compounds having thioether groups.

Mercaptans, thioethers, di- and polysulfides and their use as lubricant additives are known from the U.S. Pat. No. 4,246,127.

Various additives are in general added to lubricants to improve the performance characteristics of the lubricants. Since lubricants require a high load-carrying capacity for transmitting large forces, there are added to them so-called high-pressure and anti-wear additives, by virtue of which the wear-phenomena otherwise occurring are greatly reduced. When on the other hand oxygen and moisture for example simultaneously act on a metal surface, corrosion can occur, and it is for this reason that corrosion inhibitors are added to prevent these substances having access to the metal surface. Oxidation reactions in a lubricant occurring at elevated temperature to a greater extent as a result of atmospheric oxygen can for example be inhibited by the addition of antioxidants. It is known that certain substances, used as additives for lubricants, can combine a number of such properties and are hence known as "multipurpose additives". Such substances are obviously in great demand for economic and practical reasons.

The compounds of this invention combine some of these properties.

The present invention relates also to compositions containing a lubricant or a hydraulic fluid and at least one compound of the formula I $$R-S-CH_2-CH(OH)-CH_2-S-R^4 \quad (I)$$

in which R can be a radical of the form

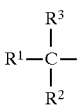

wherein $R^1$, $R^2$ and $R^3$ independently of one another are each $C_1-C_{18}$-alkyl and together contain no more than 22 C atoms, and $R^2$ and $R^3$ are in addition hydrogen, or wherein R is $C_5-C_6$-cycloalkyl, phenyl or naphthyl unsubstituted or substituted by $C_1-C_4$-alkyl, or is benzyl, furyl, thienyl, morpholinyl, imidazolyl, thiazolyl, oxazolyl, imidazolinyl, thiazolinyl, oxazolinyl, benzimidazolinyl, benzthiazolinyl or benzoxazolinyl, and wherein $R^4$ is phenyl unsubstituted or substituted by $—NH_2$, or is $C_1-C_{16}$-alkyl which is unsubstituted or substituted by phenyl, $—NH_2$, 2-oxo-pyrrolidino, cyano, perfluoro-$C_1-C_8$-alkyl or one or two OH groups, and which can be interrupted by —O— or —S—, or is $C_5-C_6$-cycloalkyl, or $R^4$ is $-(CH_2)_m-S-CH_2-CH(OH)-CH_2-S-(C_{1-16}\text{-alkyl})$, m being zero to 6, or $R^4$ is $-(CH_2)_n-C(O)-O-R^5$ wherein n is 1 or 2, and $R^5$ is hydrogen, $C_1-C_{16}$-alkyl or an alkali metal, or wherein $R^4$ is $—CH[—CO—OR^5][—CH_2—CO—OR^5]$ wherein $R^5$ has the meaning given above, or wherein $R^4$ is $-(CH_2)_r-C(O)-OH \cdot H_2N-(C_8-C_{16}\text{-alkyl})$ or $-(CH_2)_r-C(O)-OH \cdot N-(CH_2-CH_2-OH)_3$, r being 1 or 2, or is $—P(X)[-O-R^6]_2$, wherein X can be either =O or =S, and $R^6$ is $C_1-C_{16}$-alkyl, phenyl or tolyl, or wherein $R^4$ is α- or β-naphthyl, benzothiazolyl, benzimidazolyl, benzoxazolyl, thiazolyl, thiazolinyl, triazolyl, tetrazolyl, pyridyl, quinolyl, imidazolyl, imidazolinyl, oxazolinyl, $—SO_2—O—$(alkali metal), $—C_6H_4—C(O)—O—$(alkali metal), 2-oxo-4-hydroxy-3-penten-3-yl or $-(CH_2)_s-R^7$, wherein s is 1 to 4, and $R^7$ is benzoxazolyl, benzimidazolyl, benzothiazolyl, thiazolinyl, imidazolinyl or oxazolinyl, or wherein $R^4$ is $-(CH_2)_t-CO-N(R^8)(R^9)$, wherein t is 1 or 2, and $R^8$ is $C_1-C_{16}$-alkyl which can be substituted by —OH, or is phenyl, hydroxyphenyl or α-naphthyl, and $R^9$ is hydrogen or $R^8$ or wherein $R^4$ is $—CH_2—CH(OH)—CH_2—S—R^{10}$, wherein $R^{10}$ is hydrogen or $C_1-C_{16}$-alkyl, or wherein $R^4$ is a radical $—R^{11}—S—CH_2—CH(OH)—CH_2—S—R$ wherein R has the meaning given above, and $R^{11}$ is a radical $-(CH_2)_2O-(CH_2)_2O-(CH_2)_2-$, o- or m-phenylene, thiadiazol-2,5-ylene or $-(CH_2)_u-$, u being zero to 8, or a radical of the formula

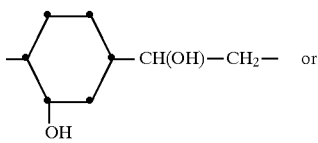

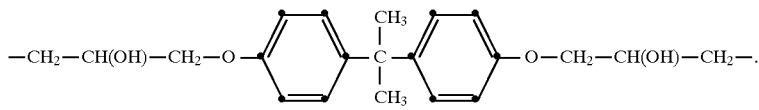

When R is a radical of the form

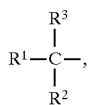

it can be

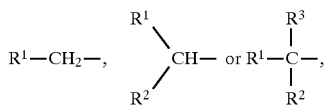

wherein $R^1$, $R^2$ and $R^3$ are each $C_{1-18}$-alkyl. For $C_1$–$C_{18}$-alkyl, the substituents are straight-chain or branched-chain, for example: methyl, ethyl, n-propyl, isopropyl, n-butyl, isobutyl, sec-butyl, tert-butyl, straight-chain or branched-chain pentyl, hexyl, heptyl, octyl, nonyl, decyl, undecyl, dodecyl, tridecyl, tetradecyl, pentadecyl, hexadecyl, heptadecyl or octadecyl. The preferred radical is

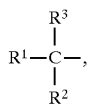

wherein $R^1$, $R^2$ and $R^3$ together with the C atom to which they are bound form $C_4$–$C_{20}$-alkyl, and none of the substituents $R^1$, $R^2$ and $R^3$ may be hydrogen. Particularly preferred is $C_4$–$C_{14}$-alkyl, and especially preferred is tert-butyl, tert-nonyl (ex Phillips Petroleum) or tert-dodecyl, by tert-dodecyl being meant for example a radical such as is described for tertiary dodecylmercaptan in "Ullmanns Enzyklopadie der technischen Chemie, 4th Edition, Vol. 23, pp. 181–182, Verlag Chemie, Weinheim".

When R is $C_5$–$C_6$-cycloalkyl, it is cyclopentyl or cyclohexyl.

If R is phenyl or naphthyl substituted by $C_1$–$C_4$-alkyl, the phenyl or naphthyl can be mono- to trisubstituted, preferably however monosubstituted; $C_1$–$C_4$-alkyl is: methyl, ethyl, n-propyl, isopropyl, n-butyl, isobutyl, sec-butyl or tert-butyl.

When $R^4$ is $C_1$–$C_{16}$-alkyl, or when a $C_1$–$C_{16}$-alkyl radical is contained in the substituents for $R^4$, such as in: —(CH$_2$)$_m$S—CH$_2$—CH(OH)—CH$_2$—S—(C$_1$–C$_{16}$-alkyl), —(CH$_2$)$_n$C(O)—O—(C$_1$–C$_{16}$-alkyl), —P(X)$\{$O—R$\}_2$ or —CH$_2$—CH(OH)—CH$_2$—S—(C$_1$–C$_{16}$-alkyl), or in the substituents for $R^5$, $R^8$ or $R^{10}$, the radicals concerned are straight-chain or branched-chain alkyl radicals, for example: methyl, ethyl, n-propyl, isopropyl, n-butyl, isobutyl, sec-butyl, tert-butyl, or straight-chain or branched-chain pentyl, hexyl, heptyl, octyl, nonyl, decyl, undecyl, dodecyl, tridecyl, tetradecyl, pentadecyl or hexadecyl; preferred radicals are isopropyl, tert-butyl, isooctyl, 2-ethylhexyl, tert-nonyl, tert-dodecyl and tert-tridecyl. By isooctyl here is meant a radical which is derived from isooctyl alcohol, and which is a mixture of differently branched octyl radicals. The definitions already given above apply for tert-nonyl as well as for tert-dodecyl.

When the meaning of $R_4$ is —(CH$_2$)$_r$C(O)—OH.H$_2$N—(C$_8$–C$_{16}$alkyl, the C$_8$–C$_{16}$-alkyl therein is a straight-chain or branched-chain substituent, for example: octyl, nonyl, decyl, undecyl, dodecyl, tridecyl, tetradecyl, pentadecyl or hexadecyl, the preferred substituent being terttridecyl. Suitable as an amine is moreover N—(CH$_2$—CH$_2$—OH)$_3$.

If $R^4$ is $C_1$–$C_{16}$-alkyl substituted by phenyl, it is preferably $C_1$–$C_4$-alkyl substituted by phenyl, the phenyl being in the terminal position; and benzyl is particularly preferred.

When $R^4$ is $C_1$–$C_{16}$-alkyl substituted by one or two OH groups, it is preferably —CH$_2$—CH$_2$—OH, —CH(OH)—CH$_2$—OH or —CH$_2$—CH(OH)—CH$_2$—OH.

And when $R^4$ is $C_1$–$C_{16}$-alkyl substituted by —NH$_2$, it is preferably —CH$_2$—CH$_2$—NH$_2$.

If $R^5$ is an alkali metal, or if the latter occurs in —SO$_2$—O—(alkali metal) or in —C$_6$H$_4$—CO—O—(alkali metal), it is preferably sodium or potassium.

Preferred compositions are those containing a lubricant or a hydraulic fluid and at least one compound of the formula II

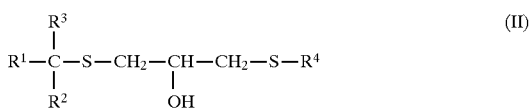

wherein $R^1$, $R^2$ and $R^3$ together with the C atom to which they are bound are $C_4$–$C_{20}$-alkyl, and none of these substituents $R^1$, $R^2$ and $R^3$ may be hydrogen, and wherein $R^4$ is phenyl unsubstituted or substituted by —NH$_2$, or is $C_1$–$C_{16}$-alkyl which is unsubstituted or substituted by phenyl, —NH$_2$, 2-oxopyrrolidino, cyano, perfluoro-$C_1$–$C_8$-alkyl or one or two OH groups, and which can be interrupted by —O— or —S—, or is $C_5$–$C_6$-cycloalkyl, or $R^4$ is: —(CH$_2$)$_m$S—CH$_2$—CH(OH)—CH$_2$—S—(C$_1$–C$_{16}$alkyl), m being zero to six, or —(CH$_2$)$_n$C(O)—O—R$^5$, wherein n is 1 or 2, and $R^5$ is hydrogen, C$_1$–C$_{16}$-alkyl or an alkali metal, or wherein $R^4$ is —CH[—CO—OR$^5$][—CH$_2$—CO—OR$^5$], wherein $R^5$ has the meaning defined above, or wherein $R^4$ is —(CH$_2$)$_r$C(O)—OH.N—C$_8$–C$_{16}$-alkyl) or —(CH$_2$)$_r$C(O)—OH.N—(CH$_2$CH$_2$—OH)$_3$, r being 1 or 2, or is —P(X)$\{$O—R$^6$]$_2$, wherein X can be either =O or =S, and $R^6$ is C$_1$–C$_{16}$-alkyl, phenyl or tolyl, or wherein $R^4$ is α- or β-naphthyl, benzothiazolyl, benzimidazolyl, benzoxazolyl, thiazolyl, thiazolinyl, pyridyl, quinolyl, imidazolinyl, oxazolinyl, —SO$_2$—O—(alkali metal), C$_6$H$_4$—C(O)—O—(alkali metal), 2-oxo-4-hydroxy-3-penten-3-yl, or —(CH$_2$)$_s$R$^7$, wherein s is 1 to 4, and $R^7$ is benzoxazolyl, benzimidazolyl, benzo-thiazolyl, thiazolinyl, imidazolinyl or oxazolinyl, or wherein $R^4$ is —(CH$_2$)$_t$CO—N(R$^8$)(R$^9$), wherein t is 1 or 2, and $R^8$ is C$_1$–C$_{16}$-alkyl which can be substituted by —OH, or is phenyl, 3-hydroxyphenyl or α-naphthyl, and $R^9$ is hydrogen or $R^8$, or wherein $R^4$ is —CH$_2$—CH(OH)—CH$_2$—S—R$^{10}$, wherein $R^{10}$ is hydrogen or C$_1$–C$_{16}$-alkyl, or wherein $R^4$ is a radical

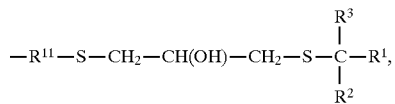

wherein $R^1$, $R^2$ and $R^3$ have the meanings defined above, and $R^{11}$ is a radical —(CH$_2$)$_2$O—(CH$_2$)$_2$O—(CH$_2$)$_2$, o- or m-phenylene, thiadiazol-2,5-ylene or —(CH$_2$)$_u$, u being zero to 8, preferably 2, or a radical of the formula

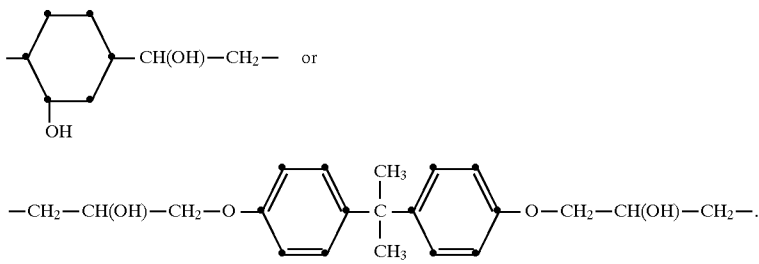

Particularly preferred are compounds containing a lubricant or a hydraulic fluid and at least one compound of the formula II in which $R^1$, $R^2$ and $R^3$ together with the C atom to which they are bound are $C_4$–$C_{20}$-alkyl, and none of these substituents $R^1$, $R^2$ and $R^3$ may be hydrogen, and wherein $R^4$ is phenyl unsubstituted or substituted by —$NH_2$, or is $C_1$–$C_{13}$-alkyl which is unsubstituted or substituted by phenyl, —$NH_2$, 2-oxopyrrolidino, cyano or one or two OH groups, and which can be interrupted by —O— or —S—, or wherein $R^4$ is –(CH$_2$)$_m$–S—CH$_2$—CH(OH)—CH$_2$—S—($C_1$–$C_{16}$-alkyl), m being zero to 4, or is –(CH$_2$)$_n$–CO—O—$R^5$, wherein $R^5$ is hydrogen, potassium or $C_4$–$C_{12}$-alkyl, and n is 1 or 2, or wherein $R^4$ is –(CH$_2$)$_r$–CO—OH.H$_2$N—($C_{10}$–$C_{16}$-alkyl), r being 1 or 2, or is —P(S)(—O—$R^6$)$_2$, wherein $R^6$ is $C^1$–$C_8$-alkyl or phenyl, or wherein $R^4$ is α-naphthyl, thiazolyl, benzothiazolyl, benzimidazolyl, benzoxazolyl, pyridyl, quinolyl or –(CH$_2$)$_s$–$R^7$, wherein s is 1 or 2, and $R^7$ is benzoxazolyl, benzimidazolyl, benzothiazolyl, thiazolinyl, imidazolinyl or oxazolinyl, or wherein $R^4$ is –(CH$_2$)$_t$–CO—N($R^8$)($R^9$), wherein t is 1 or 2, and $R^8$ is $C_1$–$C_4$-alkyl unsubstituted or substituted by —OH, or is phenyl or α-naphthyl, and $R^9$ is hydrogen or $R^8$, or wherein $R^4$ is —CH$_2$—CH(OH)—CH$_2$—S—$R^{10}$, wherein $R^{10}$ is $C_1$–$C_{14}$-alkyl, or wherein $R^4$ is a radical

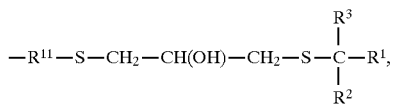

in which $R^1$, $R^2$ and $R^3$ have the meanings defined above, and $R^{11}$ is —(CH$_2$)$_2$—O—(CH$_2$)$_2$—O—(CH$_2$)$_2$—, o- or m-phenylene, thiadiazol-2,5-ylene or –(CH$_2$)$_u$, u being zero to 4, preferably 2.

More especially preferred are compounds containing a lubricant or a hydraulic fluid and at least one compound of the formula II in which $R^1$, $R^2$ and $R^3$ together with the C atom to which they are bound are $C_4$–$C_{14}$-alkyl, and none of these substituents $R^1$, $R^2$ and $R^3$ may be hydrogen, and wherein $R^4$ is phenyl, —CH$_2$—CH$_2$—NH$_2$, —CH$_2$—CH$_2$—OH, —CH$_2$—CH(OH)—CH$_2$—OH, tertiary $C_4$–$C_{14}$-alkyl, —(CH$_2$)$_2$—S—CH(OH)—CH$_2$—S—(tert-$C_8$–$C_{12}$-alkyl), —CH$_2$—COOH—, CH$_2$—CO—O—(i—$C_8H_{17}$), —CH$_2$—CO—OH.H$_2$N—(tert-$C_{10}$–$C_{16}$-alkyl), —P(S)(—O—(i—$C_3H_7$)]$_2$, —P(S)(—O—(i—$C_8H_{17}$)]$_2$, α-naphthyl, benzothiazolyl, benzimidazolyl, thiazolyl or —CH$_2$—CH(OH)—CH$_2$—S—$R^{10}$, wherein $R^{10}$ is tertiary $C_4$–$C_{14}$-alkyl, or wherein $R^4$ is a radical

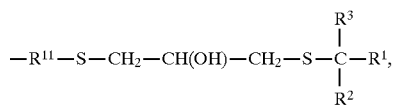

wherein $R^1$, $R^2$ and $R^3$ have the meanings defined above, and $R^{11}$ is –(CH$_2$)$_2$—O—(CH$_2$)$_2$—O—(CH$_2$)$_2$—, o-phenylene, thiadiazol-2,5-ylene or –(CH$_2$)$_u$, u being zero to 2.

Further subject matter of the present invention is formed by novel substances of the formula II in which $R^1$, $R^2$ and $R^3$ together with the C atom to which they are attached are $C_4$–$C_{20}$-alkyl, and none of these substituents $R^1$, $R^2$ and $R^3$ may be hydrogen, and wherein $R^4$ is phenyl unsubstituted or substituted by —NH$_2$, or is unsubstituted $C_1$–$C_9$-alkyl, or $C_1$–$C_{16}$-alkyl which is substituted by phenyl, —NH$_2$, 2-oxopyrrolidino, cyano, perfluoro-$C_1$–$C_8$-alkyl or one or two OH groups, and which can be interrupted by —O— or —S—, or wherein $R^4$ is –(CH$_2$)$_m$–S—CH$_2$—CH(OH)—CH$_2$—S—($C_1$–$C_{16}$-alkyl), m being zero to 6, or is –(CH$_2$)$_n$–C(O)—O—$R^5$, wherein n is 1 or 2, and $R^5$ is hydrogen, $C_1$–$C_{16}$-alkyl or an alkali metal, or wherein $R^4$ is —CH[—CO—O$R^5$][—CH$_2$—CO—O$R^5$], wherein $R^5$ has the meaning defined above, or wherein $R^4$ is –(CH$_2$)$_r$–C(O)—OH.H$_2$N—($C_8$–$C_{16}$-alkyl) or –(CH$_2$)$_r$–C(O)—OH.N(—CH$_2$—CH$_2$—OH)$_3$, r being 1 or 2, or is —P(X)(—O—$R^6$]$_2$, wherein X can be either =O or =S, and $R^6$ is $C_1$–$C_{16}$-alkyl, phenyl or tolyl, or wherein $R^4$ is α- or β-naphthyl, benzothiazolyl, benzimidazolyl, benzoxazolyl, thiazolyl, thiazolinyl, pyridyl, quinolyl, imidazolinyl, oxazolinyl, —SO$_2$—O—(alkali metal), —C$_6$H$_4$—C(O)—O—(alkali metal), 2-oxo-4-hydroxy-3-penten-3-yl or –(CH$_2$)$_s$–$R^7$, wherein s is 1 to 4, and $R^7$ is benzoxazolyl, benzimidazolyl, benzothiazolyl, thiazolinyl, imidazolinyl or oxazolinyl, or wherein $R^4$ is –(CH$_2$)$_t$–CO—N($R^8$)($R^9$), wherein t is 1 or 2, and $R^8$ is $C_1$–$C_{16}$-alkyl which is unsubstituted or substituted by —OH, or is phenyl, 3-hydroxyphenyl or α-naphthyl, and $R^9$ is hydrogen or $R^8$, or wherein $R^4$ is —CH$_2$—CH(OH)—CH$_2$—S—$R^{10}$, wherein $R^{10}$ is hydrogen or $C_1$–$C_{16}$-alkyl, or wherein $R^4$ is a radical

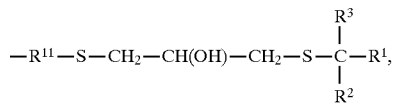

wherein $R^1$, $R^2$ and $R^3$ have the meanings defined above, and $R^{11}$ is a radical –(CH$_2$)$_2$–O–(CH$_2$)$_2$–O–(CH$_2$)$_2$–, o- or m-phenylene, thiadiazol-2,5-ylene or –(CH$_2$)$_u$, u being zero to 8, or a radical of the formula

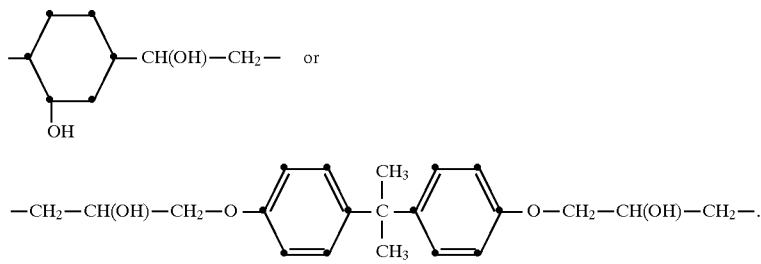

Preferred compounds of the formula II are those wherein $R^1$, $R^2$ and $R^3$ together with the C atom to which they are bound are $C_4$–$C_{20}$-alkyl, and none of these substituents $R^1$, $R^2$ and $R^3$ may be hydrogen, and wherein $R^4$ is phenyl unsubstituted or substituted by —$NH_2$, unsubstituted $C_4$–$C_9$-alkyl, or $C_1$–$C_{13}$-alkyl which is substituted by phenyl, —$NH_2$, 2-oxopyrrolidino, cyano or one or two OH groups, or is —(CH$_2$)$_m$S—CH$_2$—CH(OH)—CH$_2$—S—($C_1$–$C_{16}$-alkyl), m being zero to 4, or is —(CH$_2$)$_n$CO—O—$R^5$, wherein $R^5$ is hydrogen potassium or $C_4$–$C_{12}$-alkyl, and n is 1 or 2, or wherein $R^4$ is —(CH$_2$)$_r$CO—OH.H$_2$N ($C_{10}$–$C_{16}$-alkyl), r being 1 or 2, or is —[P(S)—]O—$R^6$]$_2$, wherein $R^6$ is $C_1$–$C_8$-alkyl or phenyl, or wherein $R^4$ is α-naphthyl, thiazolyl, benzothiazolyl, benzimidazolyl, benzoxazolyl or —(CH$_2$)$_s$$R^7$, wherein s is 1 or 2, and $R^7$ is benzoxazolyl, benzimidazolyl, benzothiazolyl, thiazolinyl, imidazolinyl or oxazolinyl, or wherein $R^4$ is —(CH$_2$)$_t$CO—N($R^8$)($R^9$), wherein t is 1 or 2, and $R^8$ is $C_1$–$C_4$-alkyl which is unsubstituted or substituted by —OH, or is phenyl or α-naphthyl, and $R^9$ is hydrogen or $R^8$, or wherein $R^4$ is —CH$_2$—CH(OH)—CH$_2$—S—$R^{10}$, wherein $R^{10}$ is $C_1$–$C_{14}$-alkyl, or wherein $R^4$ is a radical

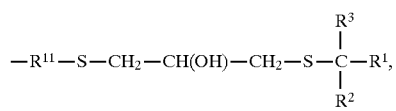

in which $R^1$, $R^2$ and $R^3$ have the meanings defined above, and $R^{11}$ is —(CH$_2$)$_2$O—(CH$_2$)$_2$O—(CH$_2$)$_2$—, o- or m-phenylene, thiadiazol-2,5-ylene or —(CH$_2$)$_u$, u being zero to 4, preferably 2,.

Particularly preferred compounds of the formula II are those wherein $R^1$, $R^2$ and $R^3$ together with the C atom to which they are bound are $C_4$–$C_{14}$-alkyl, and none of these substituents $R^1$, $R^2$ and $R^3$ may be hydrogen, and wherein $R^4$ is phenyl, —CH$_2$—CH$_2$—NH$_2$, —CH$_2$—CH$_2$—OH, —CH$_2$—CH(OH)—CH$_2$—OH, tertiary $C_4$–$C_9$-alkyl, —(CH$_2$)$_2$—S—CH$_2$—CH(OH)—CH$_2$—S—(tert-$C_8$–$C_{12}$-alkyl), —CH$_2$COOH, —CH$_2$—CO—O—(i—$C_8$H$_{17}$), —CH$_2$—CO—OH.H$_2$N—(tert-$C_{10}$–$C_{16}$-alkyl), —[P(S)—]O—(i—$C_3$H$_7$)]$_2$, —[P(S)—]O—(i—$C_8$H$_{17}$)]$_2$, α-naphthyl, benzothiazolyl, benzimidazolyl, thiazolyl or —CH$_2$—CH(OH)—CH$_2$—S—$R^{10}$, wherein $R^{10}$ is tertiary $C_4$–$C_{14}$-alkyl, or wherein $R^4$ is a radical

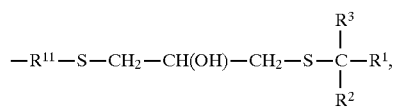

in which $R^1$, $R^2$ and $R^3$ have the meanings defined above, and $R^{11}$ is —(CH$_2$)$_2$—O—(CH$_2$)$_2$—O—(CH$_2$)$_2$—, o-phenylene, thiadiazol-2,5-ylene or —(CH$_2$)$_u$, u being zero to 2.

The following are examples of compounds of the formula I:

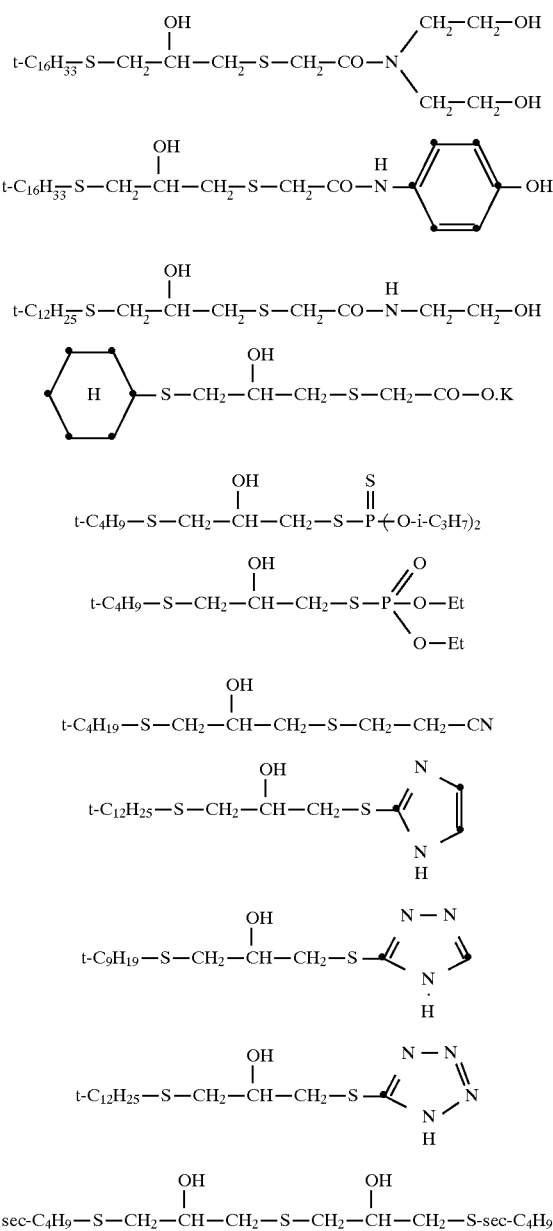

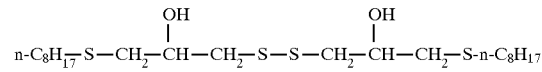

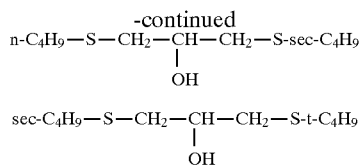

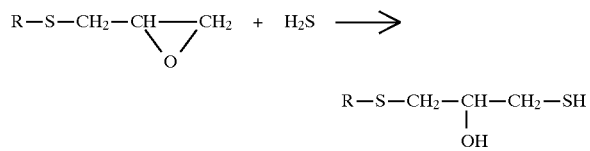

The alkyl-thiaglycidyl ethers, used as intermediates for the compounds of the formula I, are produced in the following manner:

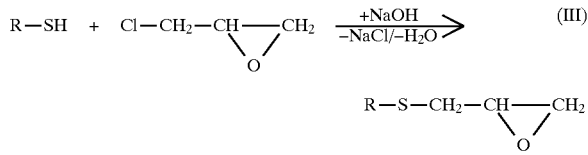

wherein the substituent R has the meanings already defined. Particularly advantageous for this reaction is the use of a phase-transfer catalyst, for example tetrabutylamine chloride. The production of alkyl-thiaglycidyl ethers is described also in the U.S. Pat. Nos. 2,965,652, 2,731,437 and BE 609,375.

The compounds of the formula I can be produced by reaction of alkyl-thiaglycidyl ethers of the formula III with a compound of the formula IV $$HS-R^4 \quad\quad (IV),$$

with the use of catalytical amounts of nucleophiles, such as sodium hydride or triethylamine, the substituents R and $R^4$ having the meanings already defined.

to α-hydroxymercaptan derivatives which yield with chlorine compounds $Cl-R^4$ the desired compounds of the formula I, the cleaved hydrogen chloride being bound by an inorganic or organic base. The oxidative coupling of α-hydroxy-mercaptan derivatives results moreover in some compounds of the formula I being obtained with a disulfide structure.

In addition, it is possible in the case of some compounds of the formula I to use also the following method of synthesis:

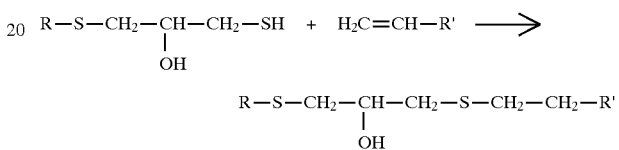

wherein —$CH_2$—$CH_2$—R' can be a radical denoted specifically by $R^4$.

Finally, an α-hydroxymercaptan compound of this kind can be reacted with a glycidyl ether, as shown by the example given below:

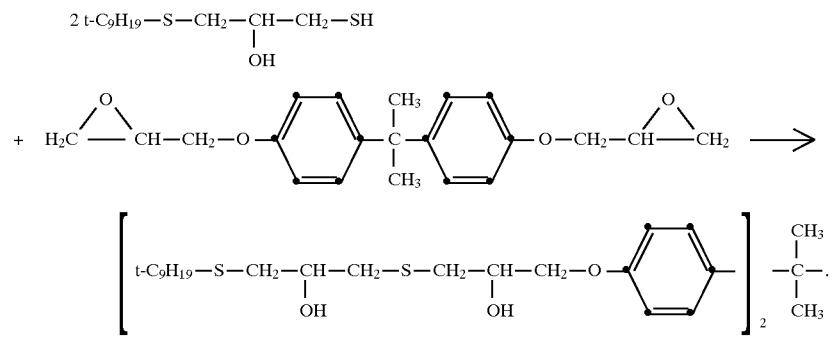

Other methods suitable for the production of compounds of the formula I are described for example in the German Offenlegungsschrift No. 2,730,414.

Another method of synthesis comprises coupling the glycidylthioether synthesis with the addition reaction of the same mercaptan:

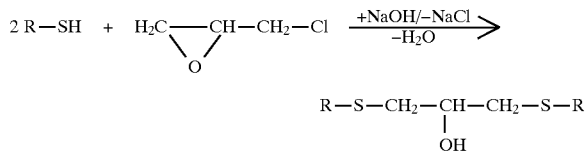

whereby some of the compounds embraced by the formula I can be produced.

A further method of synthesis proceeds by way of the following reaction:

The compounds of the formula I are of a thinly liquid, viscous to wax-like nature, and are surprisingly readily soluble in lubricants. They are particularly suitable as additives in lubricants, and result in an improvement of the high-pressure and anti-wear properties; to be emphasised also is their anti-oxidising and anticorrosive activity. In conclusion, they render possible, surprisingly, the preparation of so-called masterbatches.

The compounds of the formula I are effective even in very small amounts as additives in lubricants. They are added to the lubricants in an amount of 0.01 to 5% by weight, preferably 0.05 to 3% by weight, relative to the amount of lubricant. The lubricants concerned are familiar to a person skilled in the art, and are described for example in "Lubricants and related Products" (Schmierstoffe und verwandte Produkte) [Verlag Chemie, Weinheim, 1982]. Particularly suitable, besides mineral oils, are for example poly-α-olefins, lubricants based on esters; or phosphates, glycols, polyglycols and polyalkylene glycols.

The lubricants can additionally contain other additives which are added to further improve the basic properties of lubricants: such additives include: antioxidants, metal passivators, rust inhibitors, viscosity-index improvers, pour-point depressors, dispersants, detergents, high-pressure additives and anti-wear additives.

Examples of phenolic antioxidants
1. Alkylated monophenols
   2,6-di-tert-butyl-4-methylphenol,
   2,6-di-tert-butylphenol,
   2-tert-butyl-4,6-dimethylphenol,
   2,6-di-tert-butyl-4-ethylphenol,
   2,6-di-tert-butyl-4-ethylphenol,
   2,6-di-tert-butyl-4-n-butylphenol,
   2,6-di-tert-butyl-4-i-butylphenol,
   2,6-di-cyclopentyl-4-methylphenol,
   2-(α-methylcyclohexyl)-4,6-dimethylphenol,
   2,6-di-octadecyl-4-methylphenol,
   2,4,6-tri-cyclohexylphenol,
   2,6-di-tert-butyl-4-methoxymethylphenyl, and o-tert-butylphenol.
2. Alkylated hydroquinones
   2,6-di-tert-butyl-4-methoxyphenol,
   2,5-di-tert-butyl-hydroquinone,
   2,5-di-tert-amyl-hydroquinone, and
   2,6-diphenyl-4-octadecyloxyphenol.
3. Hydroxylated thiodiphenyl ethers
   2,2'-thio-bis(6-tert-butyl-4-methylphenol),
   2,2'-thio-bis(4-octylphenol),
   4,4'-thio-bis(6-tert-butyl-3-methylphenol), and
   4,4'-thio-bis(6-tert-butyl-2-methylphenol).
4. Alkylidene bisphenols
   2,2'-methylene-bis(6-tert-butyl-4-methylphenol),
   2,2'-methylene-bis(6-tert-butyl-4-ethylphenol),
   2,2'-methylene-bis[4-methyl-6-(α-methylcyclohexyl) phenol],
   2,2'-methylene-bis(4-methyl-6-cyclohexylphenol),
   2,2'-methylene-bis(6-nonyl-4-methylphenol),
   2,2'-methylene-bis(4,6-di-tert-butylphenol),
   2,2'-ethylidene-bis(4,6-di-tert-butylphenol),
   2,2'-ethylidene-bis(6-tert-butyl-4-isobutylphenol),
   2,2'-methylene-bis[6-(α-methylbenzyl)-4-nonylphenol],
   2,2'-methylene-bis[6-(α,α-dimethylbenzyl)-4-nonylphenol],
   4,4'-methylene-bis(2,6-di-tert-butylphenol),
   4,4'-methylene-bis(6-tert-butyl-2-methylphenol),
   1,1-bis(5-tert-butyl-4-hydroxy-2-methylphenyl)-butane,
   2,6-di-(3-tert-butyl-5-methyl-2-hydroxybenzyl)-4-methylphenol,
   1,1,3-tris-(5-tert-butyl-4-hydroxy-2-methylphenyl)-3-n-dodecyl-mercaptobutane,
   ethylene glycol-bis[3,3-bis-(3'-tert-butyl-4'-hydroxyphenyl)-butyrate],
   di-(3-tert-butyl-4-hydroxy-5-methylphenyl)-dicyclopentadiene, and
   di-[2-(3'-tert-butyl-2'-hydroxy-5'-methyl-benzyl)-6-tert-butyl-4-methyl-phenyl]terephthalate.
5. Benzyl compounds
   1,3,5-tri-(3,5-di-tert-butyl-4-hydroxybenzyl)-2,4,6-trimethylbenzene,
   di-(3,5-di-tert-butyl-4-hydroxybenzyl)sulfide,
   3,5-di-tert-butyl-4-hydroxybenzyl-mercaptoacetic acid isooctyl ester,
   bis-(4-tert-butyl-3-hydroxy-2,6-dimethylbenzyl)dithiol-terephthalate,
   1,3,5-tris-(3,5-di-tert-butyl-4-hydroxybenzyl) isocyanurate,
   1,3,5-tris-(4-tert-butyl-3-hydroxy-2,6-dimethylbenzyl) isocyanurate,
   3,5-di-tert-butyl-4-hydroxybenzyl-phosphonic acid dioctadecyl ester, and
   calcium salt of 3,5-di-tert-butyl-4-hydroxybenzyl-phosphonic acid monoethyl ester.
6. Acylaminophenols
   4-hydroxylauric acid anilide,
   4-hydroxystearic acid anilide,
   2,4-bisoctylmercapto-6-(3,5-di-tert-butyl-4-hydroxyanilino)-s-triazine, and
   N-(3,5-di-tert-butyl-4-hydroxyphenyl)carbamic acid octyl ester.
7. Esters of β-(3,5-di-tert-butyl-4-hydroxyphenyl)propionic acid with monohydric or polyhydric alcohols, for example with:
   methanol, octadecanol, 1,6-hexanediol, neopentyl glycor, thiodiethylene glycol, diethylene glycol, triethylene glycol, pentaerythritol, trishydroxyethyl isocyanurate or dihydroxyethyloxalic acid diamide.
8. Esters of β-(5-tert-butyl-4-hydroxy-3-methylphenyl) propionic acid with monohydric or polyhydric alcohols, for example with:
   methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalic acid diamide.
9. Amides of β-(3,5-di-tert-butyl-4-hydroxyphenyl) propionic acid, for example:
   N,N'-di-(3,5-di-tert-butyl-4-hydroxyphenylpropionyl) hexamethylenediamine,
   N,N'-di-(3,5-di-tert-butyl-4-hydroxyphenylpropionyl) trimethylenediamine,
   N,N'-di-(3,5-di-tert-butyl-4-hydroxyphenylpropionyl) hydrazine.
10. Examples of amine antioxidants
    N,N'-diisopropyl-p-phenylenediamine
    N,N'-di-sec-butyl-p-phenylenediamine,
    N,N'-bis(1,4-dimethylpentyl)-p-phenylenediamine,
    N,N'-bis(1-ethyl-3-methylpentyl)-p-phenylenediamine,
    N,N'-bis(1-methyl-heptyl)-p-phenylenediamine,
    N,N'-dicyclohexyl-p-phenylenediamine,
    N,N'-diphenyl-p-phenylenediamine,
    N,N'-di(naphthyl-2-)-p-phenylenediamine,
    N-isopropyl-N'-phenyl-p-phenylenediamine,
    N-(1,3-dimeethylbutyl)-N'-phenyl-p-phenylenediamine,
    N-(1-methylheptyl)-N'-phenyl-p-phenylenediamine,
    N-cyclohexyl-N'-phenyl-p-phenylenediamine,
    4-(p-toluenesulfonamido)-diphenylamine,
    N,N'-dimethyl-N,N'-di-sec-butyl-p-phenylenediamine,
    diphenylamine,
    4-isopropoxydiphenylamine,
    N-phenyl-1-naphthylamine,
    N-phenyl-2-naphthylamine,
    octylated diphenylamine, 4-n-butylaminophenol,
4-butyrylaminophenol,
4-nonanoylaminophenol,
4-dodecanoylaminophenol,
4-octadecanoylaminophenol,
di-(4-methoxyphenyl)amine,
2,6-di-tert-butyl-4-dimethylaminomethylphenol,
2,4'-diaminodiphenylmethane,
4,4'-diaminodiphenylmethane,
N,N,N,N'-tetramethyl-4,4'-diaminodiphenylmethane,
1,2-di(phenylamino)ethane,
1,2-di-[(2-methylphenyl)-amino]ethane,
1,2-di(phenylamino)propane,
(o-tolyl)biguanide,
di-[4-(1',3'-dimethylbutyl)phenyl)amine, tert-octylated N—phenyl-1-naphthylamine, and
mixture of mono- and dialkylated tert-butyl/tert-octyldiphenylamines.

Examples of metal passivators are:
for copper, for example: benzotriazole, tetrahydrobenzotriazole, 2-mercaptobenzotriazole, 2,5-dimercaptothiadiazole, salicylidene-propylenediamine and salts of salicylaminoguanidene.

Examples of rust inhibitors are:
a) organic acids, the esters thereof, metal salts and anhydrides thereof, for example: N-oleylsarcosine, sorbitan monooleate, lead naphthenate, dodecenylsuccinic acid anhydride, alkenylsuccinic acid half-ester and 4-nonylphenoxyacetic acid;
b) nitrogen-containing compounds, for example: I. primary, secondary or tertiary aliphatic or cyclo-aliphatic amines and amine salts of organic and inorganic acids, for example oil-soluble alkylammonium carboxylates; II. heterocyclic compounds, for example: substituted imidazolines and oxazolines;
c) phosphorus-containing compounds, for example: amine salts of phosphoric acid partial esters;
d) sulfur-containing compounds, for example: barium dinonylnaphthalenesulfonates and calcium petroleum sulfonates.

Examples of viscosity-index improvers are for example:
polymethacrylate, vinyl pyrrolidone/methacrylate copolymers, polybutenes, olefin copolymers and styrene/acrylate copolymers.

Examples of pour-point depressors are for example:
polymethacrylates and alkylated naphthalene derivatives.

Examples of dispersants/surfactants are for example:
polybutenylsuccinimides, polybutenylphosphonic acid derivatives, basic magnesium, calcium and barium sulfonates and phenolates.

Examples of anti-wear additives are for example:
compounds containing sulfur and/or phosphorus and/or halogen, such as sulfurised vegetable oils, zinc dialkyldithiophosphates, tritolylphosphate, chlorinated paraffins and alkyl- and aryldisulfides.

The compounds according to the invention are used as additives for lubricant systems, especially motor oils. In lubricant systems they exhibit: high-pressure, anti-wear, antioxidising and corrosion-inhibiting activity. A particular advantage of these compounds, in contrast to compounds having comparable properties, is that they are free from phosphorus and tin, as a result of which the aftercombustion of the exhaust gases is also not impaired. Furthermore, these compounds do not contain any hydrolytically or solvolytically cleavable bonds and are therefore also particularly stable.

The following Production Examples are given in order to further illustrate the invention, the Examples 1 to 3 concerning intermediates for producing the compounds of the formula I, and the Examples 4 to 41 describing these compounds of the formula I.

EXAMPLE 1

(cf. Table 1) Tert-octylglycidyl thioether

A solution of 66 parts by weight of sodium hydroxide, 300 parts by weight of water and 8 parts by weight of tetrabutylammonium chloride is added dropwise at 15° to 20° C. in the course of 70 minutes, with stirring and partial cooling (especially at the commencement of the addition), to a mixture of 219 parts by weight of tert-octylmercaptan and 135 parts by weight of epichlorohydrin. The reaction mixture is further stirred for 1 hour at 50° C.; the aqueous phase is then separated, and the organic phase is washed with 200 parts by weight of water. The organic phase is finally distilled in vacuo to thus obtain the tert-octylglycidyl thioether in the form of a colourless liquid having a boiling point of 74° to 75° C. at 0.02 mbar, and a refractive index of $n_D^{20}=1.4803$; the yield is 250 parts by weight, which corresponds to 82% of the theoretical yield.

EXAMPLE 4

(cf. Table 1)

27.1 parts by weight of tert-dodecylglycidyl thioether are added dropwise at 50°–60° C., with stirring, to a mixture of 7.8 parts by weight of 2-mercaptoethanol and catalytical amounts of sodium hydride (exothermic reaction). After completion of the addition, stirring is continued at the same temperature for 1 hour, and the following compound is thus obtained as a yellow viscous liquid having a refractive index of $n_D^{20}=1.5132$ in a yield of 100%.

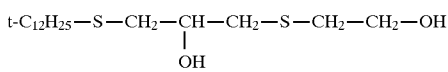

EXAMPLES 2 AND 3 AND 5–41

Compounds 2 and 3 (Examples 2 and 3) are prepared by a method analogous to that of Example 1, and compounds 5 to 41 are prepared by a method analogous to that of Example 4.

TABLE 1

| Example No. | Formula | Observations | Boiling point (°C.) | $n_D^{20}$ |
|---|---|---|---|---|
| 1 | t-$C_8H_{17}$—S—$CH_2$—CH(—O—)$CH_2$ (epoxide) | colourless liquid | 74–75° C./at 2.66 Pa | 1.4803 |
| 2 | t-$C_9H_{19}$—S—$CH_2$—CH(—O—)$CH_2$ (epoxide) | colourless liquid | 81–82° C./at 1.33 Pa | 1.4800 |
| 3 | t-$C_{12}H_{25}$—S—$CH_2$—CH(—O—)$CH_2$ (epoxide) | colourless liquid | 100–102° C./at 1.33 Pa | 1.4800 |
| 4 | t-$C_{12}H_{25}$—S—$CH_2$—CH(OH)—$CH_2$—S—$CH_2$—$CH_2$—OH | viscous liquid | | 1.5132 |
| 5 | t-$C_{12}H_{25}$—S—$CH_2$—CH(OH)—$CH_2$—S—$CH_2$—CH(OH)—$CH_2$—OH | viscous liquid | | 1.5115 |
| 6 | t-$C_{12}H_{25}$—S—$CH_2$—CH(OH)—$CH_2$—S-t-$C_{12}H_{25}$ | viscous liquid | | 1.4958 |
| 7 | t-$C_{12}H_{25}$—S—$CH_2$—CH(OH)—$CH_2$—S—$CH_2$—CO—O-i-$C_8H_{17}$ | viscous liquid | | 1.4905 |
| 8 | t-$C_{12}H_{25}$—S—$CH_2$—CH(OH)—$CH_2$—S—$CH_2$—$C_6H_5$ | viscous liquid | | 1.5331 |
| 9 | t-$C_{12}H_{25}$—S—$CH_2$—CH(OH)—$CH_2$—S—$CH_2$—$CH_2$—S—$CH_2$—CH(OH)—$CH_2$—S-t-$C_{12}H_{25}$ | viscous liquid | | 1.5210 |
| 10 | t-$C_{12}H_{25}$—S—$CH_2$—CH(OH)—$CH_2$—S—S—$CH_2$—CH(OH)—$CH_2$—S-t-$C_{12}H_{25}$ | | | |
| 11 | t-$C_{12}H_{25}$—S—$CH_2$—CH(OH)—$CH_2$—S—P(=S)(O-i-$C_3H_7$)$_2$ | viscous liquid | | 1.5049 |
| 12 | t-$C_{12}H_{25}$—S—$CH_2$—CH(OH)—$CH_2$—S—P(=S)(O-i-$C_8H_{17}$)$_2$ | | | 1.5056 |
| 13 | t-$C_{12}H_{25}$—S—$CH_2$—CH(OH)—$CH_2$—S—(benzothiazol-2-yl) | viscous liquid | | 1.5650 |
| 14 | t-$C_{12}H_{25}$—S—$CH_2$—CH(OH)—$CH_2$—S—$CH_2$—CO—OH·$H_2$N-t-$C_{13}H_{27}$ | viscous liquid | | 1.4982 |
| 15 | t-$C_{12}H_{25}$—S—$CH_2$—CH(OH)—$CH_2$—S—C(=N—N=)—S—$CH_2$—CH(OH)—$CH_2$—S-t-$C_{12}H_{25}$ (1,3,4-thiadiazole-2,5-diyl linkage) | viscous liquid | | 1.5590 |

TABLE 1-continued

| Example No. | Formula | Observations | Boiling point (°C.) | $n_D^{20}$ |
|---|---|---|---|---|
| 16 | t-C$_{12}$H$_{25}$—S—CH$_2$—CH(OH)—CH$_2$—S—(CH$_2$)$_2$—O—(CH$_2$)$_2$<br>t-C$_{12}$H$_{25}$—S—CH$_2$—CH(OH)—CH$_2$—S—(CH$_2$)$_2$—O | colourless liquid | | 1.5221 |
| 17 | t-C$_8$H$_{27}$—S—CH$_2$—CH(OH)—CH$_2$—S-t-C$_8$H$_{17}$ | colourless liquid | 133–135° C./ at 2.66 Pa | 1.5010 |
| 18 | t-C$_8$H$_{17}$—S—CH$_2$—CH(OH)—CH$_2$—S—CH$_2$—CH$_2$OH | viscous liquid | | 1.5112 |
| 19 | t-C$_8$H$_{17}$—S—CH$_2$—CH(OH)—CH$_2$—S—CH$_2$<br>t-C$_8$H$_{17}$—S—CH$_2$—CH(OH)—CH$_2$—S—CH$_2$ | viscous liquid | | 1.5298 |
| 20 | t-C$_8$H$_{17}$—S—CH$_2$—CH(OH)—CH$_2$—S—C(=N—N=)S—C—CH$_2$—CH(OH)—CH$_2$—S-t-C$_8$H$_{17}$ (thiadiazole ring) | colourless liquid | | 1.5590 |
| 21 | t-C$_8$H$_{17}$—S—CH$_2$—CH(OH)—CH$_2$—S-(benzothiazol-2-yl) | viscous liquid | | 1.5908 |
| 22 | t-C$_4$H$_9$—S—CH$_2$—CH(OH)—CH$_2$—S-t-C$_4$H$_9$ | colourless liquid | 88–92° C./ at 3.99 Pa | 1.4961 |
| 23 | t-C$_9$H$_{19}$—S—CH$_2$—CH(OH)—CH$_2$—S-t-C$_9$H$_{19}$ | colourless liquid | 143–147° C./ at 6.65 Pa | 1.4990 |
| 24 | Ph—S—CH$_2$—CH(OH)—CH$_2$—S—Ph | | 168–169° C./ at 2.66 Pa | 1.5392 |
| 25 | t-C$_9$H$_{19}$—S—CH$_2$—CH(OH)—CH$_2$—S—Ph | | 160–161° C. at 5.32 Pa | 1.5477 |
| 26 | t-C$_9$H$_{19}$S—CH$_2$—CH(OH)—CH$_2$—S—C$_6$H$_4$—NH$_2$ | | | 1.5638 |
| 27 | t-C$_9$H$_{19}$—S—CH$_2$—CH(OH)—CH$_2$—S—CH$_2$—CH(OH)—Ph | | | 1.5446 |

TABLE 1-continued

| Example No. | Formula | Observations | Boiling point (°C.) | $n_D^{20}$ |
|---|---|---|---|---|
| 28 | $(sec\text{-}C_4H_9\text{—}S\text{—}CH_2)_2CH\text{—}OH$ | | 97–98° C. at 5.32 Pa | 1.5000 |
| 29 | $t\text{-}C_9H_{19}\text{—}S\text{—}CH_2\text{—}\underset{\underset{OH}{\mid}}{CH}\text{—}CH_2\text{—}S\text{—}CH_2\text{—}CH_2\text{—}C_8F_{17}$ | | | 1.4179 |
| 30 | $t\text{-}C_9H_{19}\text{—}S\text{—}CH_2\text{—}\underset{\underset{OH}{\mid}}{CH}\text{—}CH_2\text{—}S\text{—}$  | | | 1.5467 |
| 31 | $t\text{-}C_9H_{19}\text{—}S\text{—}CH_2\text{—}\underset{\underset{OH}{\mid}}{CH}\text{—}CH_2\text{—}S\text{—}$  | | | 1.5845 |
| 32 | $t\text{-}C_9H_{19}\text{—}S\text{—}CH_2\text{—}\underset{\underset{OH}{\mid}}{CH}\text{—}CH_2\text{—}S\text{—}$  | | | 1.5491 |
| 33 | $n\text{-}C_{12}H_{25}\text{—}S\text{—}CH_2\text{—}\underset{\underset{OH}{\mid}}{CH}\text{—}CH_2\text{—}S\text{—}CH_2\text{—}CH_2\text{—}OH$ | solid substance | melting point 46–48° | |
| 34 | $t\text{-}C_9H_{19}\text{—}S\text{—}CH_2\text{—}\overset{\overset{OH}{\mid}}{CH}\text{—}CH_2\text{—}S\text{—}CH_2\text{—}CH_2\text{—}OH$ | | | 1.5160 |
| 35 | $t\text{-}C_9H_{19}\text{—}S\text{—}CH_2\text{—}\overset{\overset{OH}{\mid}}{CH}\text{—}CH_2\text{—}S\text{—}\overset{\overset{S}{\parallel}}{P}(\text{O-i-}C_3H_7)_2$ | | | 1.5122 |
| 36 | $t\text{-}C_9H_{19}\text{—}S\text{—}CH_2\text{—}\overset{\overset{OH}{\mid}}{CH}\text{—}CH_2\text{—}S\text{—}CH_2\text{—}CH_2\text{—}N$  | | | 1.5224 |
| 37 | $t\text{-}C_{12}H_{25}\text{—}S\text{—}CH_2\text{—}\overset{\overset{OH}{\mid}}{CH}\text{—}CH_2\text{—}S\text{—}CH_2\text{—}CH_2\text{—}N$ 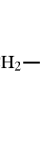 | | | 1.5143 |
| 38 | $t\text{-}C_9H_{19}\text{—}S\text{—}CH_2\text{—}\overset{\overset{OH}{\mid}}{CH}\text{—}CH_2\text{—}S\text{—}CH_2\text{—}CH_2\text{—}O\text{-}n\text{-}C_4H_9$ | | 153–156° C. at 6.65 Pa | 1.4948 |
| 39 | $t\text{-}C_{12}H_{25}\text{—}S\text{—}CH_2\text{—}\overset{\overset{OH}{\mid}}{CH}\text{—}CH_2\text{—}S\text{—}CH_2\text{—}CO\text{—}N\underset{HO\text{—}CH_2\text{—}CH_2}{\overset{HO\text{—}CH_2\text{—}CH_2}{\diagup}}$ | | | 1.5170 |
| 40 | $n\text{-}C_8H_{17}\text{—}S\text{—}CH_2\text{—}\underset{\underset{OH}{\mid}}{CH}\text{—}CH_2\text{—}S\text{—}$ 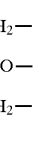 | | | 1.5830 |

TABLE 1-continued

| Example No. | Formula | Observations | Boiling point (°C.) | $n_D^{20}$ |
|---|---|---|---|---|
| 41 | t-C$_9$H$_{19}$—S—CH$_2$—CH(OH)—CH$_2$—S—CH$_2$—CO—NH—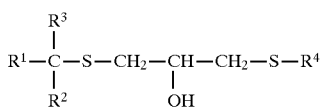 | | | 1.561 |

The following Application Example serves to further illustrate the results obtained by application of additives according to the present invention.

Application Example 1: With the Shell four-ball apparatus (IP 239/73 - Extreme pressure and wear lubricant test for oils and greases four-ball machine), the following values are obtained:

1. W.L.=Weld Load: this is the load under which the 4 balls weld together within 10 seconds.
2. W.S.D.=Wear Scar Diameter in mm.: this is the mean wear diameter with a load of 400N during 10 minutes.

A basic oil having a viscosity of ISO-VH 100 with a low content of aromatic compounds and containing 0.035% of S is used as the test fluid for determining the effectiveness of the additives.

TABLE 2

| Additive | Test with the Shell four-ball apparatus | | | |
|---|---|---|---|---|
| Example | W.L. (N) | | W.S.D. 10 min. (mm) | |
| No. (cf. Table 1) | 1% of additive | 2.5% of additive | 0.25% of additive | 1.0% of additive |
| 4 | 2200 | 2400 | 0.60 | 0.50 |
| 5 | 1800 | | | 0.75 |
| 6 | 2200 | 2400 | 0.60 | 0.50 |
| 7 | 1800 | | | 0.75 |
| 8 | 2200 | 2400 | 0.50 | 0.50 |
| 9 | 2200 | 2200 | 0.50 | 0.70 |
| 10 | 2200 | 2600 | 0.70 | 0.75 |
| 11 | 2200 | 2400 | 0.50 | 0.50 |
| 12 | 2200 | 2400 | 0.50 | 0.50 |
| 13 | 2000 | 2200 | 0.50 | 0.50 |
| 16 | 2000 | 2200 | 0.55 | 0.60 |
| 17 | 2000 | 2400 | 0.50 | 0.55 |
| 19 | 2200 | 2400 | 0.60 | 0.65 |
| 20 | 2400 | 2800 | 0.55 | 0.65 |
| 21 | 2350 | 2700 | | |
| 22 | 2000 | 2200 | 0.50 | 0.55 |
| 23 | 2000 | 2050 | | |

What is claimed is:

1. A compound of formula II $$R^1-\underset{\underset{R^2}{|}}{\overset{\overset{R^3}{|}}{C}}-S-CH_2-\underset{\underset{OH}{|}}{CH}-CH_2-S-R^4 \quad (II)$$

wherein $R^1$, $R^2$ and $R^3$ together with the C-atom to which they are bound are $C_4$–$C_{20}$-alkyl, and none of these substituents $R^1$, $R^2$ and $R^3$ may be hydrogen, and wherein $R^4$ is benzothiazolyl, —(CH$_2$)$_m$—S—CH$_2$—CH(OH)—CH$_2$—S—(C$_1$–C$_{16}$alkyl), m being zero, or —(CH$_2$)$_s$—R$^7$ wherein s is 1 to 4, and $R^7$ is benzothiazolyl.

2. A compound of formula II according to claim 1, wherein $R^1$, $R^2$ and $R^3$ together with the C-atom to which they are bound are $C_4$–$C_{14}$-alkyl, and none of these substituents $R^1$, $R^2$ and $R^3$ may be hydrogen, and wherein $R^4$ is benzothiazolyl, —(CH$_2$)$_m$—S—CH$_2$—CH(OH)—CH$_2$—S—(C$_1$–C$_{16}$alkyl), m being zero, or —(CH$_2$)$_s$—R$^7$ wherein s is 1 or 2, and $R^7$ is benzothiazolyl.

3. A compound of formula II according to claim 1, wherein $R^1$, $R^2$ and $R^3$ together with the C-atom to which they are bound are $C_4$–$C_{20}$-alkyl, and none of these substituents $R^1$, $R^2$ and $R^3$ may be hydrogen, and wherein $R^4$ is benzothiazolyl.

4. A compound of formula II according to claim 1 wherein $R^1$, $R^2$ and $R^3$ together with the C-atom to which they are bound are tert-octyl and $R^4$ is benzothiazolyl.

* * * * *